United States Patent
Racz et al.

(10) Patent No.: US 9,265,563 B2
(45) Date of Patent: Feb. 23, 2016

(54) ABLATION INSTRUMENTS AND RELATED METHODS

(75) Inventors: N. Sandor Racz, Farmers Branch, TX (US); Ricardo Ruiz-Lopez, Sant Jordi Desvalls (ES)

(73) Assignee: Custom Medical Applications, Inc., Johnstown, NY (US)

( * ) Notice: Subject to any disclaimer, the term of this patent is extended or adjusted under 35 U.S.C. 154(b) by 1844 days.

(21) Appl. No.: 12/224,321

(22) PCT Filed: Feb. 22, 2007

(86) PCT No.: PCT/US2007/004665
§ 371 (c)(1),
(2), (4) Date: Dec. 3, 2008

(87) PCT Pub. No.: WO2007/100629
PCT Pub. Date: Sep. 7, 2007

(65) Prior Publication Data
US 2009/0187179 A1 Jul. 23, 2009

Related U.S. Application Data

(60) Provisional application No. 60/775,466, filed on Feb. 22, 2006.

(51) Int. Cl.
*A61B 18/14* (2006.01)
*A61B 18/12* (2006.01)
(Continued)

(52) U.S. Cl.
CPC .............. *A61B 18/14* (2013.01); *A61B 18/1492* (2013.01); *A61B 18/1206* (2013.01);
(Continued)

(58) Field of Classification Search
CPC ........... A61B 2018/00577; A61B 2017/22038; A61B 2018/00791; A61B 2018/00815; A61B 2017/00867; A61B 28/28; A61B 2018/00702; A61B 2018/0091; A61B 17/320725; A61B 2017/00022; A61B 18/14; A61B 18/1492; A61B 18/1206; A61B 18/1477; A61B 18/18; A61B 2018/00875; A61B 2018/1425; A61B 2018/144; A61B 2018/1467; A61M 2025/0086; A61M 25/0108
USPC ........ 606/33, 41, 42, 45–50; 607/98, 99, 101, 607/102, 115, 116, 122, 154–156; 604/96.01
See application file for complete search history.

(56) References Cited

U.S. PATENT DOCUMENTS

| | | |
|---|---|---|
| 4,724,836 A | 2/1988 | Okada |
| 5,281,213 A | 1/1994 | Milder et al. |

(Continued)

FOREIGN PATENT DOCUMENTS

| | | |
|---|---|---|
| JP | 04-307055 | 10/1992 |
| WO | WO 90/07303 A | 7/1990 |

(Continued)

OTHER PUBLICATIONS

Supplementary European Search Report, EP 07 75 1430 dated Jul. 3, 2009.

(Continued)

*Primary Examiner* — Emily Schmidt
*Assistant Examiner* — Lauren M Peng
(74) *Attorney, Agent, or Firm* — TraskBritt, P.C.

(57) ABSTRACT

An ablation instrument including a body and an ablating member is provided. The body includes a distal end and a surface with the ablating member coupled toward the distal end of the body. The ablating member includes a lesion wire extending through and along a portion of the surface of the body for creating lesions in a target tissue while the body serves to isolate surrounding tissue from the target tissue. A method of ablating a target area is also provided.

21 Claims, 4 Drawing Sheets

(51) Int. Cl.
*A61B 18/18* (2006.01)
*A61B 18/00* (2006.01)

(52) U.S. Cl.
CPC ............ *A61B18/1477* (2013.01); *A61B 18/18* (2013.01); *A61B 2018/00577* (2013.01); *A61B 2018/00702* (2013.01); *A61B 2018/00791* (2013.01); *A61B 2018/00875* (2013.01); *A61B 2018/144* (2013.01); *A61B 2018/1407* (2013.01); *A61B 2018/1425* (2013.01); *A61B 2018/1467* (2013.01)

(56) References Cited

U.S. PATENT DOCUMENTS

| | | |
|---|---|---|
| 5,281,215 A | 1/1994 | Milder |
| 5,342,292 A | 8/1994 | Nita et al. |
| 5,350,375 A | 9/1994 | Deckelbaum et al. |
| 5,415,901 A | 5/1995 | Tanaka et al. |
| 5,423,807 A | 6/1995 | Milder |
| 5,486,161 A | 1/1996 | Lax et al. |
| 5,542,916 A | 8/1996 | Hirsch et al. |
| 5,549,644 A | 8/1996 | Lundquist et al. |
| 5,562,720 A | 10/1996 | Stern et al. |
| 5,588,432 A | 12/1996 | Crowley |
| 5,613,950 A | 3/1997 | Yoon |
| 5,653,692 A | 8/1997 | Masterson et al. |
| 5,667,488 A | 9/1997 | Lundquist et al. |
| 5,667,490 A | 9/1997 | Keith et al. |
| 5,681,336 A | 10/1997 | Clement et al. |
| 5,728,143 A | 3/1998 | Gough et al. |
| 5,762,626 A | 6/1998 | Lundquist et al. |
| 5,766,171 A | 6/1998 | Silvestrini |
| 5,766,190 A | 6/1998 | Wulfman |
| 5,769,880 A | 6/1998 | Truckai et al. |
| 5,807,309 A | 9/1998 | Lundquist et al. |
| 5,807,383 A | 9/1998 | Kolesa et al. |
| 5,837,001 A | 11/1998 | Mackey |
| 5,840,031 A | 11/1998 | Crowley |
| 5,843,020 A | 12/1998 | Tu et al. |
| 5,891,094 A | 4/1999 | Masterson et al. |
| 5,916,227 A | 6/1999 | Keith et al. |
| 5,931,835 A | 8/1999 | Mackey |
| 5,938,658 A | 8/1999 | Tu |
| 5,938,670 A | 8/1999 | Keith et al. |
| 5,948,009 A | 9/1999 | Tu |
| 5,954,665 A | 9/1999 | Ben-Haim |
| 5,964,756 A | 10/1999 | McGaffigan et al. |
| 5,971,983 A | 10/1999 | Lesh |
| 5,976,165 A | 11/1999 | Ball et al. |
| 5,997,534 A | 12/1999 | Tu et al. |
| 6,004,269 A | 12/1999 | Crowley et al. |
| 6,012,457 A | 1/2000 | Lesh |
| 6,024,740 A | 2/2000 | Lesh et al. |
| 6,036,689 A | 3/2000 | Tu et al. |
| 6,066,132 A | 5/2000 | Chen et al. |
| 6,080,171 A | 6/2000 | Keith et al. |
| 6,113,615 A | 9/2000 | Wulfman |
| 6,117,101 A | 9/2000 | Diederich et al. |
| 6,126,667 A | 10/2000 | Barry et al. |
| 6,135,996 A | 10/2000 | Kolesa et al. |
| 6,146,378 A | 11/2000 | Mikus et al. |
| 6,156,031 A | 12/2000 | Aita et al. |
| 6,161,548 A | 12/2000 | Tu |
| 6,164,283 A | 12/2000 | Lesh |
| 6,165,206 A | 12/2000 | Tu |
| 6,183,487 B1 | 2/2001 | Barry et al. |
| 6,200,311 B1 | 3/2001 | Danek et al. |
| 6,221,087 B1 | 4/2001 | Anderson et al. |
| 6,238,389 B1 | 5/2001 | Paddock et al. |
| 6,245,064 B1 | 6/2001 | Lesh et al. |
| 6,246,896 B1 | 6/2001 | Dumoulin et al. |
| 6,251,104 B1 | 6/2001 | Kesten et al. |
| 6,254,599 B1 | 7/2001 | Lesh et al. |
| 6,267,781 B1 | 7/2001 | Tu |
| 6,270,509 B1 | 8/2001 | Barry et al. |
| 6,280,437 B1 | 8/2001 | Pacala et al. |
| 6,283,951 B1 | 9/2001 | Flaherty et al. |
| 6,283,955 B1 | 9/2001 | Pacala et al. |
| 6,283,962 B1 | 9/2001 | Tu et al. |
| 6,299,623 B1 | 10/2001 | Wulfman |
| 6,305,378 B1 | 10/2001 | Lesh |
| 6,328,750 B1 | 12/2001 | Berry et al. |
| 6,352,534 B1 | 3/2002 | Paddock et al. |
| 6,361,531 B1 | 3/2002 | Hissong |
| 6,364,876 B1 | 4/2002 | Erb et al. |
| 6,383,151 B1 | 5/2002 | Diederich et al. |
| 6,393,314 B1 | 5/2002 | Watkins et al. |
| 6,416,511 B1 | 7/2002 | Lesh et al. |
| 6,451,009 B1 | 9/2002 | Dasilva et al. |
| 6,451,011 B2 | 9/2002 | Tu |
| 6,471,697 B1 | 10/2002 | Lesh |
| 6,482,203 B2 | 11/2002 | Paddock et al. |
| 6,482,216 B1 | 11/2002 | Hiblar et al. |
| 6,502,576 B1 | 1/2003 | Lesh |
| 6,514,247 B1 | 2/2003 | McGaffigan et al. |
| 6,514,249 B1 | 2/2003 | Maguire et al. |
| 6,514,250 B1 | 2/2003 | Jahns et al. |
| 6,522,930 B1 | 2/2003 | Schaer et al. |
| 6,527,769 B2 | 3/2003 | Langberg et al. |
| 6,558,382 B2 | 5/2003 | Jahns et al. |
| 6,592,575 B1 | 7/2003 | Kesten et al. |
| 6,595,989 B1 | 7/2003 | Schaer |
| 6,641,580 B1 | 11/2003 | Edwards et al. |
| 6,669,693 B2 | 12/2003 | Friedman |
| 6,692,450 B1 | 2/2004 | Coleman |
| 6,695,782 B2 | 2/2004 | Ranucci et al. |
| 6,706,041 B1 | 3/2004 | Costantino |
| 6,752,805 B2 | 6/2004 | Maguire et al. |
| 6,764,486 B2 | 7/2004 | Natale |
| 6,813,520 B2 | 11/2004 | Truckai et al. |
| 6,830,568 B1 | 12/2004 | Kesten et al. |
| 6,849,075 B2 | 2/2005 | Bertolero et al. |
| 6,852,109 B2 | 2/2005 | Winston et al. |
| 6,855,144 B2 | 2/2005 | Lesh |
| 6,872,205 B2 | 3/2005 | Lesh et al. |
| 6,887,238 B2 | 5/2005 | Jahns et al. |
| 6,893,436 B2 | 5/2005 | Woodard et al. |
| 6,923,801 B2 | 8/2005 | Kurtzer et al. |
| 6,926,713 B2 | 8/2005 | Rioux et al. |
| 6,955,173 B2 | 10/2005 | Lesh |
| 6,958,062 B1 | 10/2005 | Gough et al. |
| 7,033,352 B1 | 4/2006 | Gauthier et al. |
| 2003/0023285 A1 | 1/2003 | Eggers et al. |
| 2004/0054369 A1* | 3/2004 | Nelson et al. ............... 606/41 |
| 2004/0243056 A1* | 12/2004 | Rowland ............... A61B 18/10 604/96.01 |

FOREIGN PATENT DOCUMENTS

| | | |
|---|---|---|
| WO | WO 96/10961 | 4/1996 |
| WO | WO 97/06739 A2 | 2/1997 |
| WO | WO 97/32525 | 9/1997 |
| WO | WO 98/02201 | 1/1998 |
| WO | WO 2007/056302 A2 | 5/2007 |
| WO | WO 2007/100629 A3 | 9/2007 |

OTHER PUBLICATIONS

U.S. Appl. No. 10/694,235, filed Oct. 27, 2003, Racz et al., Safety Spinal Needle.
U.S. Appl. No. 11/886,100, filed Oct. 12, 2007, Racz et al., Catheter Connection Hub.
U.S. Appl. No. 11/981,901, filed Oct. 31, 2007, Racz et al. Method of Using Spinal Needle Assemblies.
U.S. Appl. No. 12/009,349, filed Jan. 17, 2008, N. Sandor Racz, Flow Elements for Use With Flexible Spinal Needles, Needle Assemblies and Method Therefor.
U.S. Appl. No. 12/084,529, filed Sep. 16, 2008, N. Sandor Racz, Reinforced Catheter With Articulated Distal Tip.
U.S. Appl. No. 12/154,323, filed May 21, 2008, Racz et al., Catheter Connection Hub.
PCT International Search Report, PCT/US07/04665, dated Oct. 31, 2007.

* cited by examiner

ABLATION INSTRUMENTS AND RELATED METHODS

PRIORITY CLAIM

This application claims the benefit of the filing date of U.S. Provisional Patent Application Ser. No. 60/775,466, filed Feb. 22, 2006, for "Ablation Instruments and Related Methods," the contents of which are incorporated by this reference.

TECHNICAL FIELD

Embodiments of the invention generally relate to medical devices such as ablation instruments and related methods of use.

BACKGROUND

Current surgical procedures utilizing catheters are generally extremely disruptive and may cause a great deal of damage to healthy tissue. Quite typically, the desired target area is very small, or relatively small, while the ablation end or edge of the catheter is much larger, causing unneeded damage. In recent years, development of products has been directed with an emphasis on minimizing the traumatic nature of traditional surgical procedures.

Various types of ablation instruments exist in the prior art, including mechanical, electrical, thermal, radio frequency. Conventionally, the various types of ablation instruments have specified uses and/or specialties allowing various methods/procedures to be used with the various types of ablation instruments.

These conventional instruments use catheter-based heat sources for the intended purpose of inducing thrombosis and controlling hemorrhaging within certain body lumens. Detailed examples of local energy delivery devices and related procedures such as those of the types described above are disclosed in the following references: U.S. Pat. No. 4,672,962; U.S. Pat. No. 4,676,258; U.S. Pat. No. 4,790,311; U.S. Pat. No. 4,807,620; U.S. Pat. No. 4,998,933; U.S. Pat. No. 5,035,694; U.S. Pat. No. 5,190,540; U.S. Pat. No. 5,226,430; U.S. Pat. No. 5,292,321; U.S. Pat. No. 5,449,380; U.S. Pat. No. 5,505,730; U.S. Pat. No. 5,558,672; U.S. Pat. No. 5,562,720; U.S. Pat. No. 4,449,528; U.S. Pat. No. 4,522,205; U.S. Pat. No. 4,662,368; U.S. Pat. No. 5,078,736; and U.S. Pat. No. 5,178,618, the contents of which are incorporated by this reference.

Other conventional devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue-device interface either as another temperature control mechanism as a carrier or medium for the localized energy delivery. Examples of ablation devices which use fluid to assist in electrically coupling electrodes to tissue are disclosed in the following references: U.S. Pat. No. 5,348,554; U.S. Pat. No. 5,423,811; U.S. Pat. No. 5,505,730; U.S. Pat. No. 5,545,161; U.S. Pat. No. 5,558,672; U.S. Pat. No. 5,569,241; U.S. Pat. No. 5,575,788; U.S. Pat. No. 5,658,278; U.S. Pat. No. 5,688,267; U.S. Pat. No. 5,697,927; U.S. Pat. No. 5,722,403; U.S. Pat. No. 5,769,846; PCT Patent Application Publication No. WO 97/32525; and PCT Patent Application Publication No. WO 98/02201, the contents of which are incorporated by this reference.

Other examples of conventional mechanical devices use a probe as a surgical device in order to allow the physician to directly apply an electrode to tissue. Detailed examples of surgical probes are disclosed in the following references: U.S. Pat. No. 6,023,638; U.S. Pat. No. 4,841,979; U.S. Pat. No. 4,917,096; and U.S. Pat. No. 6,152,920, the contents of which are incorporated by this reference.

While U.S. Pat. No. 5,766,190 discloses a rotating mechanical, or rotational ablation device wherein one or more diamond plated burrs are attached to a driveshaft, which rotates at high speed driven by an advancer/turbine assembly, the contents of which are incorporated by this reference. The driveshaft is provided with a quick connection/disconnection feature allowing for removal of the burr/driveshaft assembly portion of the device from the advancer turbine assembly portion of the device.

As well, other medical devices are known for removing abnormal deposits from corporal channels. For example, U.S. Pat. No. 4,990,134, and U.S. Pat. No. 4,445,509 describe a rotating mechanical system for removing plaque from an artery, the contents of which are incorporated by this reference. U.S. Pat. No. 4,990,134 discloses the use of an ellipsoidal cutting head, or burr, coated with abrasive material such as tiny diamond chips. The cutting head rotates at such a tip velocity that the cutting head generates microscopic particles (on the order of 5 microns or less) and leaves behind a tissue base having a smooth appearance on the surface of the wall of the vessel from which an abnormal deposit has been removed.

Further, U.S. Pat. No. 5,938,670 discloses an ablation device that includes a releasably joinable drive and catheter assemblies, the contents of which are incorporated by this reference. The drive assembly includes a tachometer assembly and a regulator for monitoring and controlling ablating burr speed. Various embodiments disclose an ablating burr that is operatively connected to a catheter tube by drive gears or releasable threads. A radiopaque member is included on the distal end of the catheter tube rendering it visible to an observer.

U.S. Pat. No. 6,527,769 discloses an ablation device assembly which is adapted to form a conduction block along a length of tissue between two predetermined locations along the left atrial wall, the contents of which are incorporated by this reference. The assembly comprises an ablation element on an elongated ablation member that is coupled to each of two delivery members allowing the delivery members to controllably position and secure the ablation element along the length of tissue between the predetermined locations. A linear lesion in the tissue between the predetermined locations is then formed by actuation of the ablation element. Also, the ablation member may slideably engage one or two delivery members such that an adjustable length of the ablation element along the ablation member may be extended externally from the engaged delivery member and along a length of tissue.

Further, surgical procedures also utilize electromagnetic ablation devices.

U.S. Pat. No. 6,958,062 discloses a multiple antenna ablation apparatus including an electromagnetic energy source, a trocar including a distal end, and a hollow lumen extending along a longitudinal axis of the trocar, and a multiple antenna ablation device with three or more antennas, the contents of which are incorporated by this reference. The antennas are initially positioned in the trocar lumen as the trocar is introduced through tissue. At a selected tissue site the antennas are deployable from the trocar lumen in a lateral direction relative to the longitudinal axis. Each of the deployed antennas has an electromagnetic energy delivery surface of sufficient size to, (i) create a volumetric ablation between the deployed antennas, and (ii) the volumetric ablation is achieved without impeding out any of the deployed antennas when 5 to 200 watts of electromagnetic energy is delivered from the electromagnetic energy source to the multiple antenna ablation device. The multiple antenna ablation device is connected to the electromagnetic energy source by a cable.

U.S. Pat. No. 5,785,705 discloses an radio frequency (RF) ablation apparatus that has a delivery catheter with a delivery catheter lumen and a delivery catheter distal end, the contents of which are incorporated by this reference. A first RF electrode is positioned in the delivery catheter lumen. The first RF electrode has a distal end, RF conductive surface, and a lumen. A second RF electrode has a distal end. The second RF electrode is at least partially positioned in the lumen of the first catheter, with its distal end positioned at the exterior of the first RF electrode distal end. An RF power source is coupled to the first and second RF electrodes.

U.S. Pat. No. 5,843,020 discloses an RF ablation device that has a delivery catheter with distal and proximal ends, the contents of which are incorporated by this reference. A handle is attached to the proximal end of the delivery catheter. The delivery catheter has an electrode deployment system whereby the electrode includes a retractable tip section comprising a deployable electrode with portion of one side having a sharp edge.

U.S. Pat. No. 6,508,815 discloses an apparatus and method for use in performing ablation of organs and other tissues includes a radio frequency generator which provides a radio frequency signal to ablation electrodes, the contents of which are incorporated by this reference. The power level of the radio frequency signal is determined based on the subject area of ablation. The radio frequency signal is coupled with the ablation electrodes through a transformation circuit. The transformation circuit includes a high impedance transformation circuit and a low impedance transformation circuit. The high or low impedance transformation circuit is selected based on the impedance of the ablation electrodes in contact with the subject tissue. Measurements of vacuum level, impedance level, resistance level, and time are monitored during an ablation procedure. Values outside of established parameters operate to stop the ablation procedure.

Further descriptions of RF ablation electrode designs conventionally known are disclosed in U.S. Pat. No. 5,209,229; U.S. Pat. No. 5,487,385; and WO 96/10961. the contents of which are incorporated by this reference. Still further, other conventional energy emitting ablation elements are disclosed in U.S. Pat. No. 4,641,649 (microwave ablation); and U.S. Pat. No. 5,156,157 (laser ablation), the contents of which are incorporated by this reference.

Conventional concern in perform surgical procedures includes ensuring that the ablation procedure is complete and not overdone. Complete ablation procedure includes extending ablation through the thickness of the tissue to be ablated before the application of ablation energy is stopped. U.S. Pat. No. 6,648,883 refers to this cut/ablation depth/completion as "transmural" ablation, the contents of which are incorporated by this reference. Conventional methods for detecting transmural ablation include monitoring a desired drop in electrical impedance at the electrode site as disclosed in U.S. Pat. No. 5,562,721, the contents of which are incorporated by this reference. Other indicators are disclosed in U.S. Pat. No. 5,558,671 and U.S. Pat. No. 5,540,684.

A factor in lesion size is tissue temperature. Accordingly, a thermistor or thermal sensor is commonly used to monitor the probe temperature in an effort to monitor the eventual lesion size. RF lesion heat is generated within the tissue; the temperature monitored will be the resultant heating of an electrode or probe by the lesion. A temperature gradient may extend from the lesion to the probe tip, so that the probe tip is slightly cooler than the tissue immediately surrounding it, but substantially hotter than the periphery of the lesion because of the rapid attenuation of heating effect with distance within the lesion.

U.S. Pat. No. 6,648,883 discloses a system and method for creating lesions and assessing their completeness or transmurality by monitoring the impedance of the tissue being ablated, the contents of which are incorporated by this reference. The system monitors for an impedance measurement that is stable at a predetermined level for a certain time, rather than attempting to detect a desired drop or a desired or increased impedance.

In these conventional devices, current spreads out radially from the electrode tip, so that current density is greatest next to the tip, and decreases progressively at distances from it. The frictional heat produced from ionic agitation is proportional to current, i.e., ionic density. Therefore, the heating effect is greatest next to the electrode and decreases further from it.

However, difficulties still exist in surgical or other procedures requiring application of ablation to a target area. In RF lesion ablation, a high frequency alternating current flows from the electrode into the tissue. Tissue heat generated is produced by the flow of current through the electrical resistance offered by the tissue. The greater this resistance, the greater the heat generated.

Accordingly, a need exists for an ablation instrument that can provide greater access and precision to the target area while providing a partial isolation of the target area.

DISCLOSURE OF THE INVENTION

Generally, embodiments of the invention relate an ablation instrument for use with systems for ablating. The ablation instrument includes a body having a proximal end and a distal end, and an ablating member about the distal end of the body. The ablating member includes a lesion wire extending along at least a portion of at least one side surface of the body.

Various embodiments of the invention may generally comprise structures including, but not limited to, needles, catheters and other probes for implementing the ablation instrument. Embodiments of the invention may comprise an energy source electrically coupled to the ablation instrument. Energy sources of embodiments of the invention comprise radio frequency (RF), microwave radiation, an inductively coupled RF fields, ultrasound, shortwave, and thermal conduction, including combinations of the aforementioned for example and without limitation.

Further embodiments may optionally comprise a thermal sensor to measure temperature and/or impedance of the lesion wire, target area and sensitive tissue area, including combinations thereof. Such measurements may be used to control the procedure.

Still further embodiments may generally include methods of ablating a target tissue. One method includes the steps of inserting an ablation instrument with a body and an ablating member into a patient, orienting the ablation instrument's ablating member about a target tissue of the patient, and ablating the target tissue, advantageously while the body of the ablation instrument partially isolates the target tissue. Another method optionally includes measuring the temperature of an ablating member, the temperature of a target area, or the impedance of a target area.

The ablation instruments of embodiments of the invention are useful in procedures such as rhizotomy, pulmonary ablation, organ ablation, nerve end ablation for example. Generally, the embodiments of the invention find general applicability in ablation procedures for allowing an operator to partially isolate a target tissue during an ablation procedure.

Other advantages and features of the invention will become apparent when viewed in light of the description of the various embodiments of the invention when taken in conjunction with the attached drawings and appended claims.

MODE(S) FOR CARRYING OUT THE INVENTION

While the invention will be described with reference to various embodiments, the description is illustrative of the invention and is not to be construed as limiting the invention.

As used herein, the term "ablate" or "ablation," including derivatives thereof, is generally the substantial altering of the mechanical, electrical, chemical, or other structural nature of tissue(s). In context of ablation applications shown and described with reference to the variations of the illustrative device below, "ablation" may include sufficient altering of tissue properties to substantially block conduction of electrical signals from or through the ablated tissue(s).

As used herein, the term "body" is generally the longitudinal framework of a device.

As used herein, the term "body space" may include cavities or lumens within the body which is defined at least in part by a tissue wall. For example, the cardiac chambers, the uterus, the regions of the gastrointestinal tract, and the arterial or venous vessels are all considered illustrative examples of body spaces within the intended meaning.

As used herein, the term "cannula" includes a small tube inserted into a body cavity, tissue, and/or the like for draining off fluid, ablating tissue(s), or introducing medication/other device.

As used herein, the term "lumen," including derivatives thereof, is generally any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

As used herein, the term "needle" may include a longitudinally extending probe.

As used herein, the term "rhizotomy" means and refers to a process comprising the surgical severance of nerve roots and may also include a process that includes severance of spinal nerve roots or any surgical procedure in which nerve roots are cut to relieve intractable pain or to stop severe muscle spasms.

As used herein, the term "trocar" includes a cutting instrument or cutting head primarily used for insertion of a catheter into or through a tissue, lumen, etc. Trocars are conventionally triangular shaped cutting heads; however, the shape of the cutting head may vary.

In general, embodiments of the invention relate to ablation instruments and related methods of use comprising all types of medical devices, including cardiovascular access catheters, coronary catheters, endoscopic catheters, surgical catheters, and ablation needles for example and without limitation. More particularly, embodiments of the ablation instruments and related methods of use of the invention help to mitigate excessive damage to a target area, such as a tissue, lumen, for example, by allowing a user, such as a physician, to deliver or transmit an energy source more directly to a target area while at least partially isolating the target area from other tissue.

In certain embodiments of the invention, an ablation instrument generally includes a body having a proximal end and a distal end and an ablating member, wherein the ablating member includes a lesion wire extending along a portion of at least one side surface of the body. Lesion wires of the various embodiments of the invention are electrically coupled to an energy source. In operation of the various devices and methods of the invention, a circuit is created which includes a lesion wire(s), a power source, and a patient's body (not shown in the Figures). Further electrical elements may also be included, such as, but not limited to, electrodes, ground patch, further instruments, monitors, and/or the like. While the invention is primarily directed toward an ablation instrument, including a method of use, it is recognized that systems, i.e., power sources, connection cables or other instrumentalities, for implementing the invention are particularly known to those of ordinary skill in the art. Accordingly, the embodiments of the invention that follow are directed at embodiments of the ablation instrument and no further attention will directed toward a system for implementing an ablation instrument because the reference as cited above give numerous examples of conventional systems adequate for utilizing the invention herein.

Figure 1:
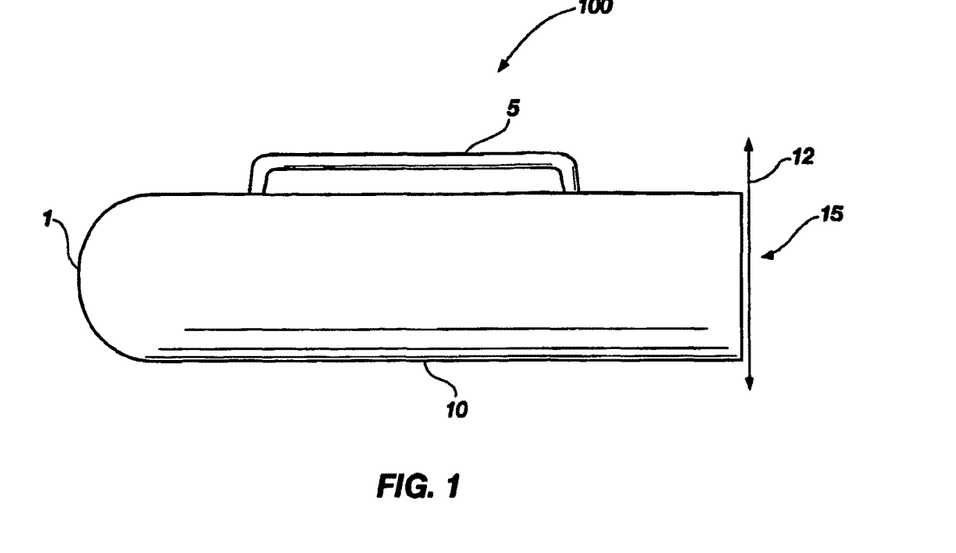
FIG. 1 is an illustration of an ablation instrument in accordance with an embodiment of the invention.
Figure 7:
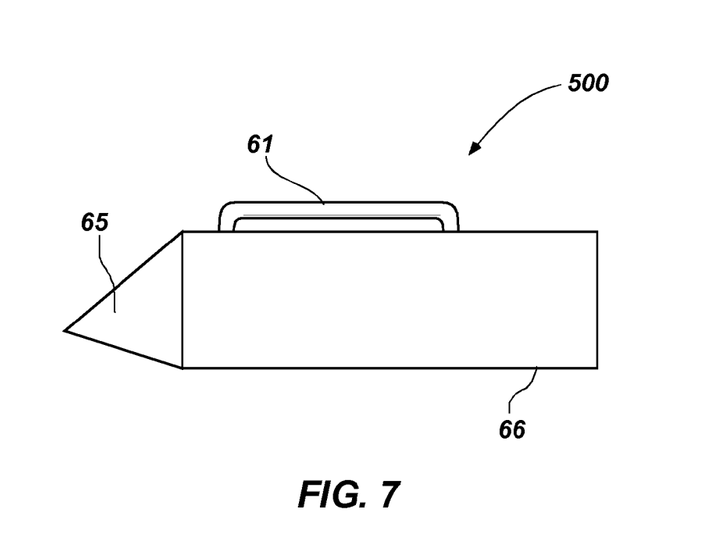
FIG. 7 is an illustration of an ablation instrument in accordance with a still further embodiment of the invention.

Now referring to the figures, FIG. 1 is an illustration of an ablation instrument 100 in accordance with an embodiment of the invention. FIG. 1 illustratively shows a tip portion 01 of the ablation instrument 100. The ablation instrument 100 generally comprises a body 10 and a lesion wire 5. The tip 1 of body 10 is generally considered a blunt tip that helps to guide the ablation instrument into place when used. However, the shape of the tip 1 may vary according to desired applications. For example and not by way of limitation, depending upon the particular application of the ablation instrument, the tip 1 may be smooth, burred, blunt, sharp or any other desired texture and/or shape. In various embodiments, a tip may optionally comprise a trocar (not shown). A trocar may be a separate element attached to the tip 1. Also, the tip 1 may be shaped or formed as a trocar. In various embodiments, the tip 1 may be configured to induce a magnetic field, resonance or excited response in a magnetically susceptible tissue for example to allow monitoring or imaging of the tissue area being ablated. An embodiment of the invention utilizing a trocar is illustrated in FIG. 7.

The tip 1 may further include a guidance means or system. Suitable examples of a guidance means for embodiments of the invention may include MRI systems, video systems, fluoroscopic guidance, stereotactic guidance techniques, CT imaging, and ultrasound, for example. However, in various embodiment, guidance means may be located either elsewhere in the body or proximate to the body. Suitable, but not limiting examples of guidance systems that may be used with embodiments of the invention are disclosed in U.S. Pat. No. 6,960,351 and U.S. Pat. No. 6,960,215.

The body 10 of the ablation instrument 100 includes a diameter and an effective length that depends on the particular medical procedure being performed and may be varied or selected accordingly. In general, the body 10 may include conventional sizes ranging from 1 mm to several centimeters in diameter which are contemplated with the embodiments of the invention, and may include sizes larger or smaller than conventionally used as is appropriate for ablation desired. In general, the length of the ablation instrument 100 ranging from millimeters to a few meters in length is contemplated with the embodiments of the invention.

The body 10 may include any insulative material and may be coated with an insulative material. In various embodiments, the body 10 may include plastic or polyalkyl, such as, but not limited, including a polyimide, a polyethylene, a polyvinyl chloride, a fluoroethylpolymer (FEP), a polytetrafluoroethylene (PTFE), a polyolefin, a latex rubber, a silicone tubing, a nylon tubing, a copolymer, and combinations of materials for example. The material of the body 10 may exhibit properties such as relatively elastic, expandable and tubular and may include other attributes appropriate for like kind instruments. However, the particular type of material used in construction of the body 10 would be of routine skill in the art. The body 10 may also be formed to be flexible, semi-flexible, or rigid. In general, embodiments of the invention for intravasculature use may be constructed with a more flexible body, such as a catheter, whereas an embodiment suitable for a procedure such as a laparoscopic ablation of organs/tissue would tend to use a more rigid device, such as a needle.

The body 10 of the ablation instrument 100 has a substantially cylindrical side surface. However, the body 10 may have sides of any shape, such as, but not limited to triangular, octagonal, oval, quadrangular, and/or the like.

The ablation instrument 100 includes a connection 15 that may be a connection of any type for connecting a tip portion and a body to an ablation instrument system (not shown). Examples of suitable connections include, but are not limited to, interference fits, screw on, latch, a smooth connection, and/or the like. Further embodiments integrate the tip portion with the remaining portion of the ablation instrument system such that there is not a separate tip portion, i.e., it is continuous. The line 12 is demonstrative that the FIG. 1 is not necessarily an illustration of the entire ablation instrument system and further components may be included in the ablation instrument system, such as, but not limited to further catheter length, a power source, a wire, an operator, a computer, and/or the like. Embodiments of the invention may further comprise an articulated distal tip as disclosed in patent application number PCT/US06/43224 (filed Nov. 3, 2006) titled "Reinforced Catheter with Articulated Distal Tip," published as United States Patent Application Publication US 2009/0043299 A1, and is incorporated by reference herein.

The energy source (not shown) of an ablating member utilized as part of the ablation instrument 100 may vary according to application of the system together with the ablation instrument chosen for a particular procedure. In certain embodiments, the energy source of the ablating member is radio frequency (RF) member and/or a pulsed RF member. In an alternate embodiment, the energy source of the ablating member is microwave radiation. In an alternate embodiment, the energy source of the ablating member is an inductively coupled RF fields. In an alternate embodiment, the ablating member is ultrasound. In an alternate embodiment, the energy source is shortwave. In an alternate embodiment, the energy source of the ablating member is a simple thermal conduction wire, needle and/or the like. Further embodiments may comprise combinations of one or more of the aforementioned energy sources.

The ablating member of the ablation instrument includes a lesion wire 5 is coupled to an energy source through a wire or other electrically conductive material. The lesion wire 5 may include electrically conductive material made of gold, aluminum, tungsten, nickel, titanium, platinum, stainless, copper, and brass, for example and without limitation, and may further include materials suitable as is know by one of ordinary skill in the art. The insulative properties of body 10 shield the ablating member in order to allow energy to be conveyed from the energy source through the conductive material of the lesion wire 5 and through the intended target area, when in use. The lesion wire 5 is located proximate the body 10 for improving application of energy upon the intended target area while minimizing the affect to other tissue when in use.

Figure 2:
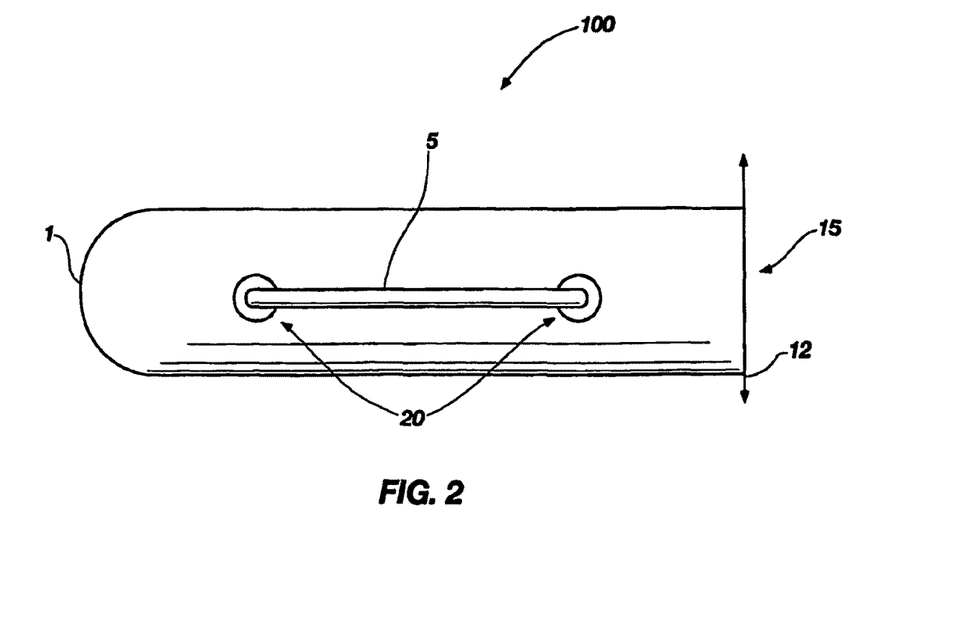
FIG. 2 is an illustration of a side perspective of the embodiment of FIG. 1.

FIG. 2 is a side perspective of the embodiment of FIG. 1. The lesion wire 5 extends across the body 10 through infusion port(s) 20. The lesion wire 5 extends along a side surface of the body 10 such that lesion wire 5 is at least partially isolated from at least one other side surface of the body 10. The infusion port(s) 20 may be of any structure and generally are present to allow access out of and across the body 10 providing electrical coupling of the lesion wire 5 with an energy source.

Figure 3:
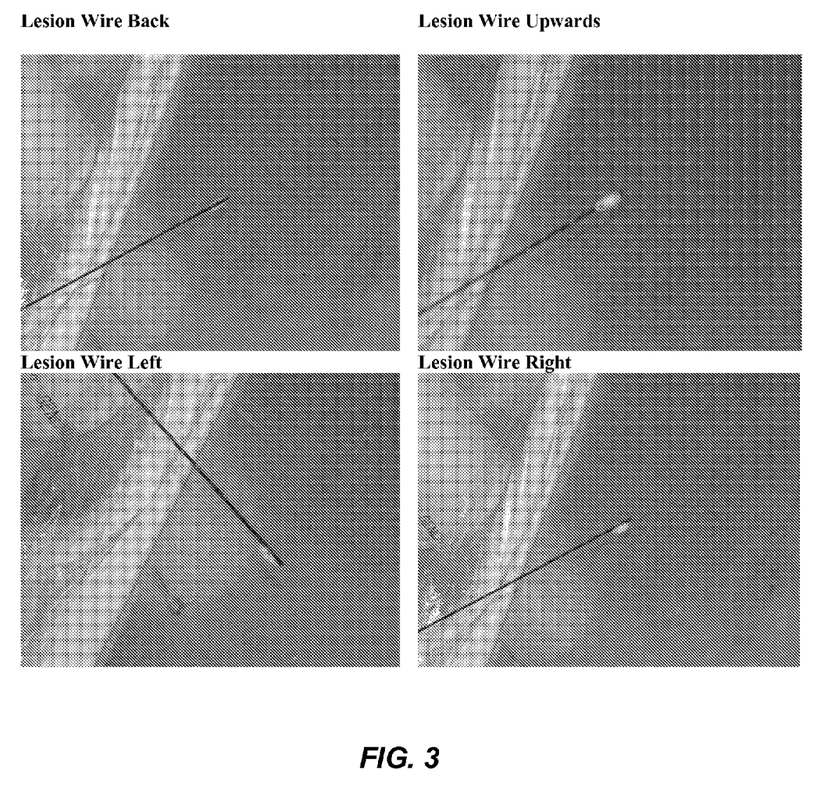
FIG. 3 is an illustration of four photographs showing a lesion that was created using an embodiment of the invention in four relative orientations.

FIG. 3 is an illustration of four photographs showing a lesion that was created using an embodiment of the invention in four relative orientations during an ablation procedure. Each of the four boxes illustrate an embodiment of an ablation instrument of the invention inserted into an egg white solution and activated such that an RF energy source ablates a target area portion of the egg white solution creating a lesion, thereby cooking the egg white solution in the target area, but not in the area at least partially isolated by the body, as is visible in each illustration. The upper left box is an illustration of a photograph of an ablation instrument of the invention wherein a lesion wire is extending along a side surface of the body. In this illustration, the body is rotated down. Activation of the ablation instrument ablates only the egg white solution adjacent to the lesion wire. Accordingly, the lesion wire extending along at least one side surface of the body isolates the target area, thereby protecting or not targeting areas adjacent to the target area. The upper right box is an illustration of an ablation instrument wherein the body is rotated such that the lesion wire is rotated up. The lower left box is an illustration of an ablation instrument wherein the body is rotated such that the lesion wire is rotated left showing ablation of a different target area. The lower right box is an illustration of an ablation instrument wherein the body is rotated such that the lesion wire is rotated right in order to isolate a different target area. As can be seen from the four illustrations, embodiments of the invention allow an operator to ablate a target area and at least partially isolate other areas.

Figure 4:
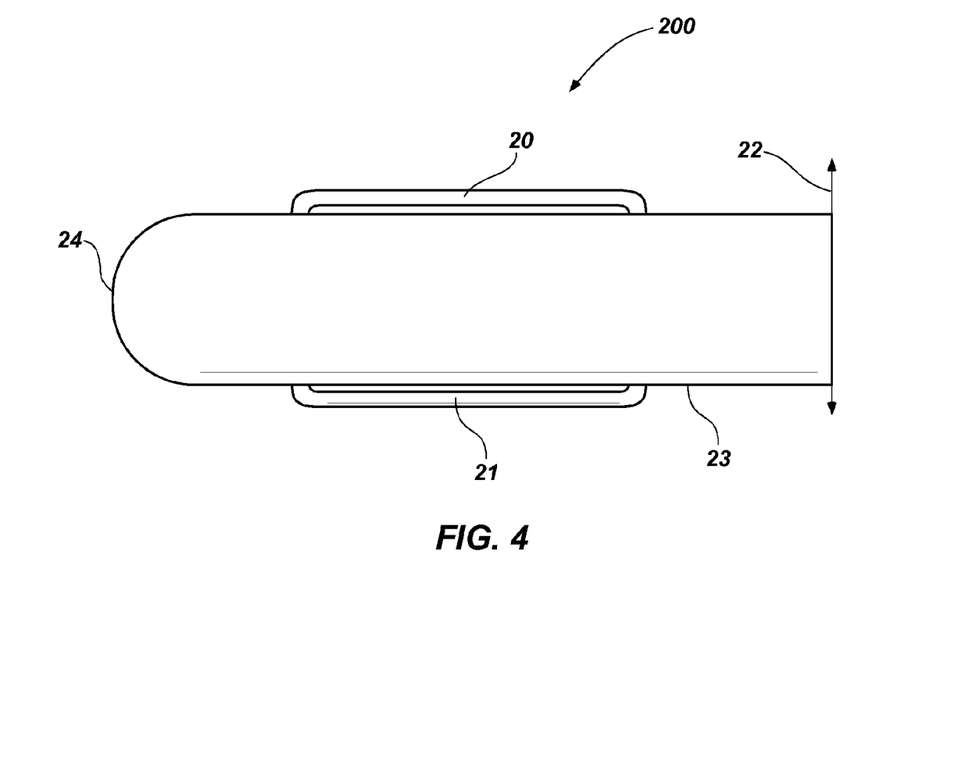
FIG. 4 is an illustration of an ablation instrument in accordance with another embodiment of the invention.

FIG. 4 is an illustration of an ablation instrument 200 in accordance with another embodiment of the invention. The ablation instrument 200 includes a tip portion 24, a lesion wires 20 and 21. The multiple lesion wires 20 and 21 allow for multiple target areas to be ablated simultaneously. The lesion wire 20 extends axially along an outer surface of the body 23 and the lesion wire 21 extends along body 23 in another axial direction. The lesion wire 20 and lesion wire 21 are circumferentially apart from one another. However, lesion wire 20 and lesion wire 21 may have any orientation along body 23 being axially or radially aligned with the body 23.

In various situations, a desired lesion or cut in a patient's body may be larger than a body of the ablation instrument of the invention. One option would be to place a second lesion wire on the opposite side of the body to create a lesion or cut that would be large and/or flat. Such a process could be used to form larger lesions in target areas where the risk of collateral damage to surrounding structures is small. The larger or pancake lesion allow for a smaller tip on an ablation instrument and the use of a small tip is helpful in maneuvering an ablation instrument in or to tight spaces. The line 22 is demonstrative that the embodiment shown in FIG. 4 is not necessarily an illustration of the entire ablation instrument 200 and further components may be included in the ablation instrument 200.

Figure 5:
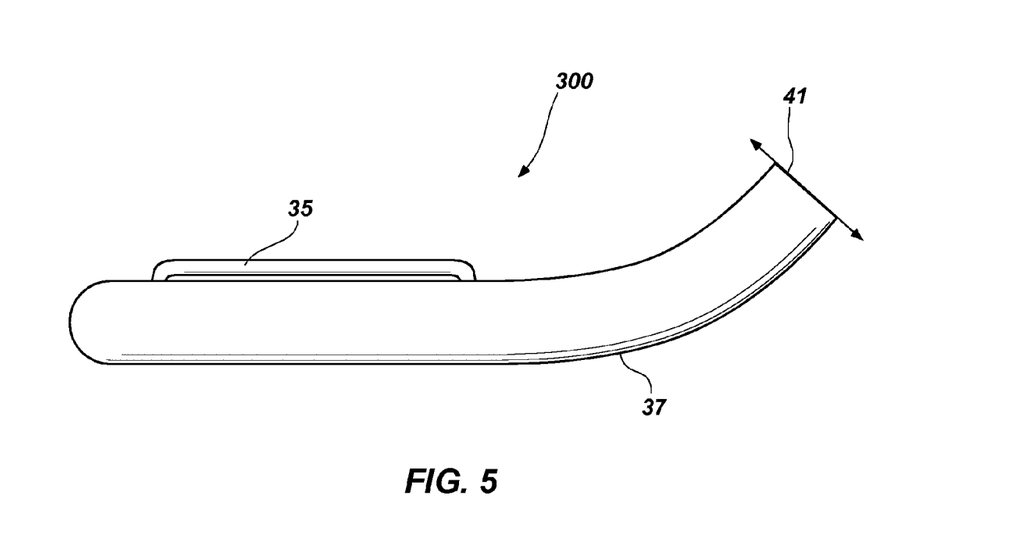
FIG. 5 is an illustration of an ablation instrument in accordance with yet another embodiment of the invention.

FIG. 5 is an illustration of an ablation instrument 300 in accordance with yet another embodiment of the invention. The ablation instrument includes a body 37 that is bent or arcuate allowing facilitation and placement upon a tissue. Optionally, the body 37 may be flexible. Flexibility can be accomplished through spiral cutting, or relief cuts when the body 37 is made from metal in order that the tip may flex and the lesion wire 35 may be placed/guided directly upon a target area. Wherein the body 37 is made from a conductive material, the lesion wire 35 will necessarily be insulated from the body 37 through the lesion ports (not shown). The line 41 is demonstrative that the embodiment shown in FIG. 5 is not necessarily an illustration of the entire ablation instrument 300 and further components may be included in or with the ablation instrument 300.

Figure 6:
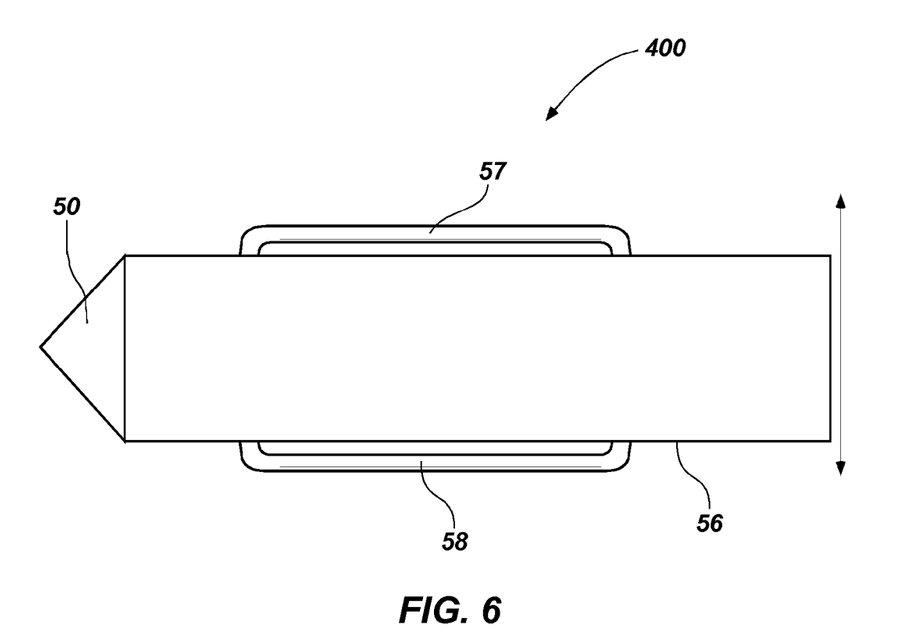
FIG. 6 is an illustration of an ablation instrument in accordance with a further embodiment of the invention.

FIG. 6 is an illustration of an ablation instrument 400 in accordance with a further embodiment of the invention. The ablation instrument includes a tip portion 50, a lesion wire 57 and a sensor 58. The lesion wire 57 extends along an external side surface of the body 56. The sensor 58 along another side surface of the body 56 and is a thermal sensor. The sensor 58 may be coupled to the body 56 so that it is positioned along a sensitive area or at any location, or proximate to any location, where monitoring is desired. Temperature of the area/tissue about the thermal sensor 58 may be monitored to ensure that damage is not being done to the sensitive portions about or outside the target area being ablated. The ablation system may include certain temperature set points and/or a certain impedance set points in order to allow the ablation instrument to be set to disconnect or discontinue all power to the lesion wire 57 of the ablation member. The set points may also be used to trigger an alarm and/or other notification.

In this embodiment, the tip 50 is illustrated with a sharp projection. The tip 50 may be metal or any other sharp or rough surface to assist in inserting the body 56 into tissue. The tip 50 may optionally be encrusted with sharp chips, such as diamond chips to aid in cutting or piercing into a tissue or a lumen. In other optional embodiments, the tip 50 may be a non-conductive tip, such as, but not limited to a ceramic or thermoplastic tip.

FIG. 7 is an illustration of an ablation instrument 500 in accordance with a still further embodiment of the invention. The ablation instrument 500 includes a body 66, a trocar 65 and a lesion wire 61.

Various embodiments further comprise one or more monitor means, such as impedance monitors and/or thermal sensors (if a thermal sensor or like device is being used) can be used in conjunction with embodiments of the invention. Impedance monitors can be used to confirm, before an ablation event, that good coupling of energy is achieved and can be used to monitor for when an ablation event is completed, as is disclosed in U.S. Pat. No. 6,648,883. Thermal sensors used with various embodiments may be of conventional design, including but not limited to thermistors, thermocouples, resistive wires, and the like.

As indicated above, a power supply means conveys energy to an ablation instrument of the invention. In various embodiments, a multiplexer can be included to measure current, voltage and temperature. A multiplexer can be driven by a controller, which in turn can be a digital or analog, or a computer with software, as is common in the art. A suitable coupling system is disclosed in U.S. Pat. No. 5,437,277. However, coupling an energy source of an ablation instrument of the invention is common in the art and various methods, systems and embodiments would be apparent to one of ordinary skill in the art.

In an embodiment, an operator means interfaces with controls and, in some embodiments, an operator interfaces with a display. The controller can be coupled to various imaging systems, transducers, thermal sensors, as well as viewing optics and fibers. The measurements of current and voltage can be used to calculate impedance.

Various embodiments also include a feedback measurement means capability that can be a measurement of impedance and/or temperature that occurs either at a thermal sensor or at the energy source.

Various embodiments of an ablation instrument of the invention further comprise an electrode deployment means. The electrode deployment system or means generally comprises a retractable tip section, which comprises the distal part of a body comprising a distal deployable and/or removable electrode which is joined to the tip section with a spring-loaded joint or a further distal deployable electrode(s), such that there are multiple deployable elements. In various embodiments, the lesion wire is deployable from the body.

Various embodiments of the invention further comprise a transceiver module means in the control system that produces pulses which are amplified by an amplifier, such as, but not limited to an RF amplifier, and supplied to a magnet assembly that produces signals radiated by the excited nuclei in the patient and may be sensed by the same lesion wire. The NMR (nuclear magnetic resonance) signals are manipulated, as is common in the art, to produce an image.

Further embodiments comprise mechanical, hydraulic, electrical, physical means to rotate at least the tip portion of the body. Suitable examples of means to rotate are disclosed in U.S. Pat. No. 5,766,190 and U.S. Pat. No. 6,752,805, generally comprising motors, valves, wires, lines, and the like, the contents of which are incorporated by this reference.

Further embodiments of the invention also contemplate methods of use generally comprising inserting an ablation instrument to a target area, isolating the target area through controlling the direction of an ablation member, and ablating the target area. Further embodiments comprise the steps of energizing the power source.

Further embodiments of methods of ablating a target tissue of the invention generally comprise the steps of a method of ablating a target tissue, comprising the steps of inserting an ablation instrument with a body and an ablating member into a patient, orienting the ablation instrument's ablating member about a target tissue, and ablating the target tissue, wherein the ablation instrument's body at least partially isolates the target tissue.

Operation of the various embodiments of the invention will create a lesion predominantly in one direction in and/or along a target area. In various embodiments, at least a portion of the body at least partially isolates tissue(s) or other target areas through a physical separation. Multiple lesion wires will act to ablate multiple target areas and an instrument can be constructed according to the claims of the invention to at least partially isolate multiple target areas.

Further embodiments of methods of the invention generally comprise positioning a thermal sensor means about a sensitive area whereby the impedance and/or temperature of or about the sensitive area is monitored during an ablation procedure. In such embodiments, optionally, a method of operation further comprises stopping the ablation procedure if a certain temperature and/or impedance is recorded and/or measured by the thermal sensor.

Exemplary medical procedures for which various embodiments of the invention are well adapted comprise rhizotomy, pulmonary ablation, organ ablation, nerve end ablation/electrical nerve stimulation, tumor ablation, cauterizing tissue, coagulation of inner vertebral disc material, sealing of ruptured, cracked, and leaky outer vertebral disc surface, and/or the like.

Embodiments of the invention include a radio frequency ablation needle. The ablation needle is a blunted needle cannula that is completely insulated with a material such as PET that minimizes stray RF energy from being transmitted to surrounding tissue while providing RF energy at the target site where a lesion is created by a lesion element externally attached to the blunted needle cannula. The lesion element is a lesion wire or lesion ribbon that passes through two holes in the cannula and is insulated to expose RF energy to one side of the cannula while insulating the other side of the cannula. The lesion wires may then extend within the cannula and back toward a proximate end thereof where they may be coupled to an energy source. Other configuration may include welding the lesion wires to a metal cannula or molding the wires in a plastic cannula. It is recognized that the conductivity of the ablation needle will depend upon the conductive path required for a particular selection of materials and the energy source chosen as would be recognized a person of ordinary skill in the art.

While particular embodiments of the invention have been shown and described, numerous variations and other embodiments will occur to those of ordinary skill in the art. Accordingly, the invention is only limited in terms of the scope of the appended claims.

What is claimed is:

1. An ablation instrument comprising:
   a rigid body having a distal end, an outer side surface, and at least two holes formed in the outer side surface of the body; and
   an ablating member coupled toward the distal end of the body, the ablating member comprising a lesion wire having an external portion extending through each hole of the at least two holes formed in the outer side surface of the body and extending externally along the outer side surface of the body in substantial alignment with an axial direction of the body spaced from the outer side surface of the body, the lesion wire for creating lesions in a target tissue and wherein the body isolates surrounding tissue from the target tissue, wherein an entirety of the lesion wire including the external portion of the lesion wire extending through each hole of the at least two holes formed in the outer side surface of the body and extending externally along the outer side surface of the body is fixed relative to the rigid body such that the entirety of the lesion wire is non-deployable from the rigid body and non-retractable into the rigid body.

2. The ablation instrument of claim 1, wherein the body is substantially cylindrical and relatively slender in an axial direction, and wherein the majority of the portion of the lesion wire extending externally along the outer side surface of the body extends along the body directly above the outer side surface of the body.

3. The ablation instrument of claim 1, wherein the body is made from a conductive material and the lesion wire of the ablating member is insulated within the body.

4. The ablation instrument of claim 1, wherein a portion of the body forming each hole of the least two holes comprises an insulative coating surrounding a portion of the lesion wire extending therethrough to electrically isolate the lesion wire from the body.

5. The ablation instrument of claim 1, further comprising a second lesion wire circumferentially spaced from the lesion wire, the second lesion wire having a portion extending through the outer side surface of the body and extending externally along the outer side surface of the body in substantial alignment with an axial direction of the body spaced from the outer side surface of the body.

6. The ablation instrument of claim 1, wherein the lesion wire is selected for radiating energy in the radio frequency (RF) electromagnetic spectrum.

7. The ablation instrument of claim 6, further comprising an energy source electrically coupled to the lesion wire and selected from the group consisting of RF, microwave radiation, an inductively coupled RF fields, ultrasound, shortwave, and thermal conductive wire.

8. The ablation instrument of claim 1, further comprising a thermal sensor for measuring at least one of an impedance about the thermal sensor and a temperature about the thermal sensor.

9. The ablation instrument of claim 1, wherein a majority of the portion of the lesion wire extending externally along the outer side surface of the body extends substantially parallel to axial direction of the body.

10. The ablation instrument of claim 1, wherein the body further comprises one of a bent and arcuate distal tip.

11. The ablation instrument of claim 1, wherein the lesion wire of the ablating member extends across the body through at least one infusion port to an electrical coupling system.

12. The ablation instrument of claim 1, further comprising a guidance system.

13. The ablation instrument of claim 1, further comprising a thermal sensor means for measuring impedance or temperature.

14. The ablation instrument of claim 1, further comprising a guidance means.

15. A method of ablating a target tissue, comprising:
   inserting the ablation instrument of claim 1 into a patient;
   orienting the ablating member of the ablation instrument about a target tissue;
   at least partially isolating surrounding tissue from the target tissue with the body of the ablation instrument; and
   ablating the target tissue.

16. The method of claim 15, further comprising measuring at least one of temperature of the ablating member, temperature of the target area, and impedance of the target area.

17. The method of claim 16, further comprising stopping ablating the target tissue when the thermal sensor measures a set point temperature and/or impedance.

18. The method of claim 15, further comprising orienting a thermal sensor about a sensitive area of the patient to monitor the temperature and/or the impedance of the sensitive area.

19. The method of claim 15, wherein inserting an ablation instrument with a body and an ablating member into a patient is for a procedure comprising at least one of rhizotomy, pulmonary ablation, organ ablation, and nerve end ablation.

20. An ablation instrument comprising:
a body having a distal end and an outer side surface; and
an ablating member coupled toward the distal end of the body, the ablating member comprising a lesion wire having a fixed external portion coupled to a portion of the body, an entirety of the lesion wire and the fixed external portion of the lesion that is external to the body being non-deployable and non-retractable relative to the body, the fixed external portion extending through the outer side surface of the body, extending externally along the outer side surface of the body in a direction substantially parallel to an axial direction of the body, and extending back through the outer side surface of the body, the lesion wire for creating lesions in a target tissue.

21. The ablation instrument of claim 20, further comprising a thermal sensor for measuring at least one of an impedance about the thermal sensor and a temperature about the thermal sensor.

* * * * *

UNITED STATES PATENT AND TRADEMARK OFFICE
CERTIFICATE OF CORRECTION

PATENT NO. : 9,265,563 B2  
APPLICATION NO. : 12/224321  
DATED : February 23, 2016  
INVENTOR(S) : N. Sandor Racz and Ricardo Ruiz-Lopez

Page 1 of 1

It is certified that error appears in the above-identified patent and that said Letters Patent is hereby corrected as shown below:

In the specification:

| | | |
|---|---|---|
| COLUMN 3, | LINE 8, | change "discloses an radio" to --discloses a radio-- |
| COLUMN 3, | LINE 25, | change "with portion" to --with a portion-- |
| COLUMN 3, | LINE 45, | change "96/10961. the" to --96/10961, the-- |
| COLUMN 4, | LINE 37, | change "relate an" to --relate to an-- |
| COLUMN 5, | LINE 3, | change "nerve end ablation" to --and nerve end ablation,-- |
| COLUMN 6, | LINES 47-48, | change "attention will directed" to --attention will be directed-- |
| COLUMN 6, | LINE 49, | change "the reference as cited" to --the references cited-- |
| COLUMN 8, | LINES 5-6, | change "member is radio" to --member is a radio-- |
| COLUMN 8, | LINE 10, | change "RF fields." to --RF field.-- |
| COLUMN 8, | LINE 23, | change "is know by" to --is known by-- |
| COLUMN 9, | LINES 3-4, | change "a lesion wires" to --and lesion wires-- |
| COLUMN 9, | LINE 55, | change "and/or a certain" to --and/or certain-- |
| COLUMN 10, | LINE 20, | change "be a digital" to --be digital-- |
| COLUMN 11, | LINE 42, | change "configuration may" to --configurations may-- |
| COLUMN 11, | LINE 47, | change "recognized a person" to --recognized by a person-- |

Signed and Sealed this  
Thirty-first Day of May, 2016

Michelle K. Lee  
*Director of the United States Patent and Trademark Office*